(12) United States Patent
Taylor

(10) Patent No.: US 7,767,291 B2
(45) Date of Patent: Aug. 3, 2010

(54) HYDROCOLLOID-CONTAINING ADHESIVE COMPOSITION HAVING NETWORK OF FIBRILLATED POLYMERIC FIBERS

(75) Inventor: Michael G. Taylor, Mundelein, IL (US)

(73) Assignee: Hollister Incorporated, Libertyville, IL (US)

( * ) Notice: Subject to any disclaimer, the term of this patent is extended or adjusted under 35 U.S.C. 154(b) by 809 days.

(21) Appl. No.: 11/687,088

(22) Filed: Mar. 16, 2007

(65) Prior Publication Data

US 2007/0219287 A1 Sep. 20, 2007

Related U.S. Application Data

(60) Provisional application No. 60/783,099, filed on Mar. 16, 2006.

(51) Int. Cl.
B32B 27/04 (2006.01)
(52) U.S. Cl. .............. 428/297.4; 428/311.51; 428/332; 602/41; 602/42; 602/43; 602/44; 602/47; 602/48; 602/52; 602/54; 602/56; 602/58
(58) Field of Classification Search .............. 428/297.4, 428/311.51, 332; 602/41, 42, 43, 44, 47, 602/48, 52, 54, 56, 58
See application file for complete search history.

(56) References Cited

U.S. PATENT DOCUMENTS

| | | | |
|---|---|---|---|
| 3,339,546 A | 9/1967 | Chen | |
| 3,743,272 A | 7/1973 | Nowotny et al. | |
| 3,848,027 A | 11/1974 | Forbess et al. | |
| 3,849,387 A | 11/1974 | Fowells et al. | |
| 3,882,095 A | 5/1975 | Fowells et al. | |
| 3,891,499 A | 6/1975 | Kato et al. | |
| 3,891,610 A | 6/1975 | Fowells | |
| 3,902,957 A | 9/1975 | Kozlowski | |
| 3,920,507 A | 11/1975 | Yonemori et al. | |
| 3,920,509 A | 11/1975 | Yonemori et al. | |
| 3,929,508 A | 12/1975 | Merz | |
| 3,991,754 A * | 11/1976 | Gertzman | 604/387 |
| 4,133,310 A * | 1/1979 | Lloyd et al. | 602/45 |
| 4,192,785 A | 3/1980 | Chen et al. | |
| 4,231,369 A | 11/1980 | Sorensen et al. | |
| 4,253,460 A | 3/1981 | Chen et al. | |
| 4,296,745 A | 10/1981 | Raymond et al. | |
| 4,367,732 A | 1/1983 | Poulsen et al. | |
| 4,551,490 A | 11/1985 | Doyle et al. | |
| 4,738,257 A | 4/1988 | Meyer et al. | |
| 4,793,337 A | 12/1988 | Freeman et al. | |
| 4,813,942 A | 3/1989 | Alvarez | |
| 4,867,748 A | 9/1989 | Samuelsen et al. | |
| 5,059,169 A | 10/1991 | Zilber | |
| 5,571,080 A | 11/1996 | Jensen | |
| 2007/0154510 A1 * | 7/2007 | Wilcher et al. | 424/422 |

OTHER PUBLICATIONS

International Search Report for International Application No. PCT/US2007/064163, dated May 28, 2008.
Written Opinion for International Application No. PCT/US2007/064163, dated May 28, 2008.
European Examination Report for Application No. 07797173.7, dated Mar. 3, 2009.

* cited by examiner

*Primary Examiner*—Bernard Lipman
(74) *Attorney, Agent, or Firm*—Marshall, Gerstein & Borun LLP

(57) ABSTRACT

Hydrocolloid-containing pressure-sensitive adhesive compositions for medical use are disclosed which contain networks of fibrillated polymeric fibers that have surface areas of at least 4 square meters per gram and which have superior properties of low cold flow and high cohesive strength.

28 Claims, No Drawings

HYDROCOLLOID-CONTAINING ADHESIVE COMPOSITION HAVING NETWORK OF FIBRILLATED POLYMERIC FIBERS

CROSS-REFERENCE TO RELATED APPLICATION

The benefit under 35 U.S.C. Section 119(e) of U.S. Provisional Patent Application Ser. No. 60/783,099, filed Mar. 16, 2006, the entire disclosure of which is incorporated herein by reference, is hereby claimed.

BACKGROUND

This invention relates to the technical field of adhesive compositions for medical dressings and skin-adhering devices such as ostomy products, wound dressings, and other medical products intended to be adhesively secured to skin surfaces of users. The invention is specifically concerned with such adhesive compositions that contain hydrocolloids and are capable of absorbing fluids and swelling as they do so.

Adhesive compositions containing hydrocolloids are well known, as disclosed, for example, in U.S. Pat. Nos. 5,571,080, 3,339,546, 4,192,785, 4,296,745, 4,367,732, 4,813,942, 4,231,369, 4,551,490, 4,296,745, 4,793,337, 4,738,257, 4,867,748, and 5,059,169, the disclosures of which are incorporated herein by reference. Hydrocolloids are commonly used in what is commonly referred to as hydrocolloid skin barriers. Such skin barriers normally include a water-insoluble pressure-sensitive adhesive as a continuous phase with particles of one or more hydrocolloids dispersed throughout the adhesive as a liquid-absorbing and swellable discontinuous phase.

The water-insoluble adhesive phase of commercial skin barriers typically consists of polyisobutylene, or block copolymers such as styrene-isoprene-styrene (SIS), or blends of these materials. The surface tack may be modified by the addition of tackifier components.

Whether a hydrocolloid composition is to be used as a skin barrier, for example, in conjunction with an ostomy appliance, or as a wound dressing, or as a paste, it should be capable of meeting several important requirements that often conflict with each other and, as a result, that currently available compositions cannot entirely meet. For instance, a composition that has relatively low viscosity favors adhesion to the skin, since the pressure-sensitive adhesive phase must be able to wet the skin and provide an adhesive bond. Low viscosity also allows the composition to track movement of the skin and maintain adhesion as the skin surface stretches and flexes. However, low viscosity may present its own problems. During product storage, the composition may exhibit cold flow, that is, it may flow beyond the perimeter of the product, whether it is a dressing or an ostomy skin barrier, and create problems in packaging and use. Such flow is more pronounced when such a composition is stored or otherwise exposed to elevated temperatures. In addition, compositions containing low viscosity pressure-sensitive adhesives may exhibit undesirably low cohesive strength.

Hydrocolloid-containing adhesive compositions, particularly skin barrier compositions of the type used for ostomy products, should also be moldable, since moldability promotes more secure adhesion to the skin by closely following skin contours. Moldability requires flow of the adhesive material with sufficient cohesive strength to maintain the physical integrity of the material when and while it is stretched. Additionally, the adhesive material should maintain its new shape after molding, without demonstrating "shape memory" that drives the material to return to its original shape. In general, current hydrocolloid skin barriers are deficient in moldability because they are too stiff to easily flow when stretched, have insufficient cohesive strength to maintain integrity when stretched, and/or have shape memory, tending to return to their original shape after being stretched.

Moldability, viscosity or flowability, surface tack, cohesive strength and liquid absorbency are all affected by the liquid-absorbing and swellable hydrocolloid content of a skin adhesive composition. Greater absorbency may be achieved with higher hydrocolloid content but quite often at the expense of reducing cohesive strength, surface tack, viscosity and/or moldability.

Jensen U.S. Pat. No. 5,571,080 discloses a hydrocolloid-containing adhesive composition in which filaments or fibers of polyethylene, or some other polymer compatible with the water-insoluble pressure-sensitive adhesive content (polyisobutylene) of the composition, is used to produce a three-dimensional mesh network that functions to retain the hydrocolloid particles even after they have become hydrated, thereby improving the wet integrity of the composition while at the same time maintaining its flexibility. The filaments or fibers may be formed by subjecting a polymeric film, such as a film of polyethylene having a thickness within the range of $20\mu$ to $200\mu$, to a shredding operation in a rotating blade mixer, although pre-formed filaments or fibers may also be used. While such a composition may have acceptable wet integrity, it still lacks sufficient moldability and has undesirable cold flow characteristics. It is an object of this invention to provide a hydrocolloid-containing skin adhesive composition that overcomes such deficiencies.

SUMMARY OF THE DISCLOSURE

An important aspect of this invention lies in providing a family of hydrocolloid-containing skinfriendly adhesive compositions which are superior to existing compositions in terms of formability or flowability during application, resistance to cold flow, and wet integrity while at the same time maintaining high surface tack. The family includes adhesive compositions over a wide range of viscosities, from relatively high viscosity skin barriers used for the adhesive attachment of ostomy pouches and other body waste collection appliances to low viscosity pastes, but all contain as essential ingredients a plastically moldable pressure-sensitive adhesive component as a continuous phase, one or more hydrocolloids in particulate form constituting a discontinuous phase and serving as a fluid-absorbing and swellable component, and fibrillated polymeric fibers forming a fibrous three-dimensional network throughout the adhesive composition. The fact that the polymeric fibers are fibrillated and have extremely high surface area for their weight (at least 4 square meters per gram ($m^2/g$), preferably 5 to 20 $m^2/g$), allows for the use of a relatively low viscosity adhesive component while still providing a composition that has surprisingly low cold flow characteristics. The fibrillated polymeric fibers provide flow control and cohesive strength to the composition. When the composition is formulated as a skin barrier, the bonding between the fibers and the pressure-sensitive adhesive component is strong enough to provide good cohesive strength, but not so strong that the composition cannot flow when stretched. Further, such a barrier does not exhibit shape memory like that observed with cross-linked barriers, so barriers formed with the compositions of this invention can be molded into different shapes before use.

By "fibrillated polymeric fibers" is meant fibers of a polyolefin or other suitable polymer that are highly branched with hair-like fibrils, the fibrils thereby greatly increasing the surface area of the fiber and the strength and integrity of the network formed in conjunction with the adhesive medium. Fibrillated polyolefin fibers of this type can be made in accordance with well known processes disclosed, for example, in U.S. Pat. Nos. 3,743,272, 3,848,027, 3,849,387, 3,882,095, 3,891,499, 3,891,610, 3,902,957, 3,920,507, 3,929,508 and 3,920,509. These patents disclose processes for the manufacture of synthetic wood pulp fiber or SWP fiber that has been used extensively in the paper industry to replace cellulose fiber. The fibrils should have average lengths within the range of about 0.1 to 3 mm and average diameters within the range of about 5 to 50μ. This fibrillated fiber content for compositions embodying the invention should fall within the range of about 0.5% to 6% of the total weight of the compositions (wt. %).

The adhesive component of the compositions of this invention may be any material that has pressure-sensitive adhesive properties with a strong affinity for the material of the fibers. It may be a single pressure-sensitive adhesive or a combination of two or more pressure-sensitive adhesives. Adhesives useful in the present invention include, for example, those based on natural rubbers, synthetic rubbers, styrene block copolymers, polyvinyl ethers, poly(meth) acrylates (including both acrylates and methacrylates), polyolefins and silicones. A particular adhesive believed to be a preferred material of choice for this invention is a polyolefin, namely, polyisobutylene (PIB), but other pressure-sensitive adhesive materials having similar properties are believed suitable.

The polymer of the fibers should be compatible with, and even have a strong affinity for, the tacky adhesive component. It has been found that polyolefins, particularly polyethylene, are highly compatible with PIB and are easily wetted by that adhesive medium. Both are non-polar saturated hydrocarbons.

Preferably such PIB is present both as medium molecular weight PIB (molecular weight in the range of about 10,000 to 40,000) and liquid or semi-liquid low molecular weight PIB (molecular weight in the range of about 1,000 to 4,000). The proportions vary depending on whether the composition is intended to be used as a moldable skin barrier (of relatively high viscosity) or as a paste (of relatively low viscosity). Thus, a moldable skin barrier for ostomy use would normally contain medium molecular weight PIB in the range of 5% to 65% wt. % and 0 wt. % to about 10 wt. % (preferably about 5 wt. %) of low molecular weight PIB.

Conversely, a paste composition, which should have low enough viscosity so that it is capable of being squeezed from a tube, would, in the absence of a diluent (see below), normally contain 0 wt. % to about 15 wt. % of medium molecular weight PIB (preferably about 10 wt. %) and about 40 wt. % to about 80 wt. % (preferably about 50 wt. %) of low molecular weight PIB. Whether used in a barrier or as a paste, the total PIB content should be at least 15 wt. %, and preferably at least 50 wt. % when no diluent (as discussed below) is present.

As indicated, the reduction in viscosity required for a paste product can alternatively (or additionally) be achieved by further ingredients designed to reduce viscosity. For example, a composition with a viscosity higher than acceptable for a paste can be diluted with an additive to yield a composition with acceptable viscosity. The diluent may be a volatile solvent that evaporates after the product is dispensed from the tube to leave a paste with higher-than-original viscosity. Alternatively, the diluent may be non-volatile so that the dispensed paste maintains a low viscosity which enables its use in a squeeze tube. Illustrative examples of diluents for this application include volatile solvents such as hexane, heptane or iso-octane and non-volatile additives such as petrolatum.

In paste compositions in which such a diluent is included to control viscosity, the weight percentages of the base ingredients (i.e., exclusive of diluents) are preferably as follows: 0 to about 65. % medium molecular weight polyisobutylene, 0 to about 10% low molecular weight polyisobutylene, about 0.5 to 6. % fibrillated polyethylene fibers, about 1 to 15% pectin, and about 1 to 30% carboxymethylcellulose, with respect to the combined weight of those base ingredients. The balance of the composition's total weight then comprises the diluent.

The hydrocolloids dispersed in the plastically moldable elastomeric adhesive phase are preferably pectin and sodium carboxymethylcellulose, although it is to be understood that other aqueous fluid absorbing and swellable hydrocolloids, such as calcium carboxymethylcellulose, carboxymethyl starches, alginates, gelatin, superabsorbents, and synthetic or natural gums, might be used. To achieve a suitable pH balance within the range of about 4 to 7 when pectin and CMC are used, the pectin content should be about 5 wt. % to about 20 wt. % (preferably about 10 wt. % to about 15 wt. %), and the CMC content should be about 5 wt. % to about 30 wt. % (preferably about 20 wt. % to about 30 wt. %). In general, the hydrocolloid content of the composition should fall within the range of about 10 wt. % to about 50 wt. %.

DETAILED DESCRIPTION OF PREFERRED EMBODIMENTS

As already noted, the surface area of fibrillated polymeric fibers is far greater than that of smooth non-fibrillated fibers, and it is the inclusion of fibrillated fibers having a surface area of at least 4 $m^2/g$, and preferably in the range of about 5 $m^2/g$ to about 20 $m^2/g$, where the benefits of this invention become apparent. Particularly effective results have been obtained with the use of fibrillated fibers of a polyolefin (polyethylene) having a surface area of about 8 $m^2/g$, available from MiniFibers, Inc. of Johnson City, Tex. The fibrils of such a material have a length within the range of about 0.55 to 0.85 mm and diameters of about 15μ. It requires only a small percentage of such material, no more than 6 wt. % of the composition as a whole, to achieve surprisingly effective results in terms of cold flow control and wet integrity, while at the same time retaining high surface tack. The inclusion of fibrillated polymeric fibers allows the use of lower viscosity PIB or other adhesive content than in typical barriers, and that in turn enhances moldability (but without significant cold flow) and allows the barrier material to flow onto the skin and adapt to body contours and changes in such contours as a user moves about.

The important aspects of the invention are further revealed by the following illustrative examples:

EXAMPLE 1

A skin barrier composition embodying this invention was prepared using 55% (by wt. % of the entire composition) medium molecular weight PIB, 5% low molecular weight PIB, 2% fibrillated polyethylene fiber (surface area of 8 $m^2/g$, fibril length about 0.55 to 0.85 mm. fibril diameter about 15μ), 13% pectin, and 25% sodium CMC. The compositions were prepared using a Brabender Type REE6 mixer at 50° C. The ingredients were added in the order given above, and after the addition of each ingredient, mixing was allowed to proceed until the mixture was homogeneous. After the final mixing period, the mixtures were removed from the mixer and allowed to equilibrate at room conditions before any testing was undertaken.

Some of the tests include compositions having the same ingredients except that monofilament polyethylene, as disclosed in U.S. Pat. No. 5,571,080, was used instead of fibrillated polyethylene. The monofilament polyethylene fibers were about 2 mm in length and 4 denier and were obtained from Engineered Fibers Technology. (The estimated surface area of the monofilament material is understood to be less than 1 $m^2/g$.)

The mixtures used in the following tests were as follows:

| Ingredient | No Fiber | Monofilament Polyethylene | Fibrillated Polyethylene | No Low Molecular Weight PIB |
|---|---|---|---|---|
| Medium Molecular Weight PIB | 57% | 55% | 55% | 60% |
| Low Molecular Weight PIB | 5% | 5% | 5% | 0% |
| Fiber (Fibrillated unless otherwise indicated) | 0% | 2% (Monofilament) | 2% | 2% |
| Pectin | 13% | 13% | 13% | 13% |
| CMC | 25% | 25% | 25% | 25% |

EXAMPLE 2

This test shows that the incorporation of fibrillated polyethylene fibers in a moldable and flowable (i.e., readily deformable) hydrocolloid-containing barrier composition greatly improves resistance to cold flow over compositions that either (1) lack any fibers or (2) have monofilament fibers instead of fibrillated fibers.

The flow properties of the test mixes were measured following ASTM C639-01, Standard Test Method for Rheological (Flow) Properties of Elastomeric Sealants. Test mixes were packed into open-end rectangular channels (¾ inch width by ½ inch high by 6 inches long) mounted on a back plate fixture. The test mixtures were trimmed so that the material was flush with all edges of the channels. Each channel fixture was placed in a 50° C. oven in vertical orientation. After 8 hours, the fixtures were removed from the oven and the positions of the bottom edges of the test mixtures were marked on the fixture plates. Each fixture was then returned to the 50° C. oven and then removed after a further 16 hours, to give a total of 24 hour oven exposure. The bottom edge for each test mixture was again marked on the fixtures. The extent of this flow was recorded for each test mixture at the 8 hour and 24 hour time points. The test results as to cold flow were as follows:

| Example | 8 Hours Flow Distance | 24 Hours Flow Distance |
|---|---|---|
| No Fiber | 41.5 mm | >50 mm |
| Monofilament Polyethylene | 9.5 mm | 13 mm |
| Fibrillated Polyethylene | 3 mm | 3 mm |

The chart reveals that a barrier composition containing 2% fibrillated polyethylene fibers was, in an 8 hour period, almost 14 time more resistant to cold flow than essentially the same composition without such fibrillated fibers, and more than 3 times more resistant than a composition containing 2% monofilament fiber. The above results of the 24 hour test were even more revealing with respect to cold flow resistance.

EXAMPLE 3

This test reveals the superior wet integrity of a barrier containing 2% fibrillated polyethylene fibers over others containing no fiber or containing 2% monofilament fibers.

The integrity of the test mixtures in a hydrated state was determined following the method described in U.S. Pat. No. 5,633,010. Test mixture samples of 0.020 inch thickness were laminated to a polyurethane backing film. Circular samples of 1.8 cm diameter were die cut, weighed, and placed in 50 mm centrifuge tubes. The samples were covered with 25 mm of phosphate buffered saline solution (pH 7.2, Sigma Chemical Co., St. Louis, Mo.) and the tubes were agitated in a horizontal orientation on a Lab Line Multi-Wrist shaker at low speed (speed setting 3) for a period of 8 hours. The intact portion of each sample remaining at the end of the test was removed from its tube, transferred to a metal pan, dried overnight at 60° C., and weighed. To obtain what may be referred to a Hydrated Integrity Values, the sample weights were corrected by subtracting the weight of the backing film from the weights measured before and after hydration. The Hydrated Integrity Value was calculated using this equation:

Integrity Value (%)=[Final Weight of Barrier]/[Initial Weight of Barrier]×100

The test yielded the following results, showing that the barrier with 2% fibrillated fibers had far greater wet integrity than either the barrier with 2% monofilament fibers or the one containing no fibers at all:

| Example | Integrity Value at 8 Hours |
|---|---|
| No Fiber | 8% |
| Monofilament Polyethylene | 51% |
| Fibrillated Polyethylene | 92% |

EXAMPLE 4

In compositions embodying this invention, liquid PIB is added as a tackifier to increase the surface tack of the barrier mixture. The following test reveals that surface tack is indeed increased by the inclusion of liquid (low molecular weight) PIB in such a barrier composition.

Tack of the test mixtures was measured following ASTM D2979-01, Standard Test Method for Pressure-Sensitive Tack of Adhesives Using an Inverted Probe Machine, with a Polyken Probe Tack Tester (Testing Machines, Inc., Ronkonkoma, N.Y., Model 80-02). Tack measurements were carried out using the spherical crown probe with a crosshead speed of 2 cm/sec and a dwell time of 10 seconds. Samples were conditioned and tested in a controlled environment room (72° F. 50% Relative Humidity).

| Example | Probe Tack, grams force |
|---|---|
| Fibrillated Polyethylene | 811 |
| No Low Molecular Weight PIB | 792 |

EXAMPLE 5

A paste composition suitable for delivery from a squeeze tube was prepared using a volatile diluent (iso-octane) to reduce the viscosity of the composition. The ingredients listed below were blended in a dual planetary mixer to achieve a homogeneous dispersion in the diluent:

| Ingredient | Weight Percent |
| --- | --- |
| Medium Molecular Weight PIB | 41.25 |
| Low Molecular Weight PIB | 3.75 |
| Fibrillated Fiber | 1.5 |
| Pectin | 9.75 |
| CMC | 18.75 |
| Iso-octane | 25.00 |

The resulting composition was readily squeezable from standard tubes.

Considering only the five base ingredients and not the diluent, the weight percentages were 55% medium molecular weight PIB, 5% low molecular weight PIB, 2% fibrillated fiber (polyethylene), 13% pectin, and 25% CMC, in relation to the combined weight of such base ingredients.

EXAMPLE 6

A paste composition suitable for delivery from a squeeze tube was prepared using a non-volatile diluent (petrolatum) to reduce the viscosity of the composition. The ingredients listed below were blended in a dual planetary mixer to achieve a homogeneous dispersion in the diluent:

| Ingredient | Weight Percent |
| --- | --- |
| Medium Molecular Weight PIB | 20.63 |
| Low Molecular Weight PIB | 1.88 |
| Fibrillated Fiber | 1.50 |
| Pectin | 4.50 |
| CMC | 9.00 |
| Petrolatum | 62.50 |

The resulting composition was readily squeezable from standard tubes.

Considering only the five base ingredients and not the diluent, the weight percentages were 55% medium molecular weight PIB, 5% low molecular weight PIB, 4% fibrillated fiber (polyethylene), 12% pectin, and 24% CMC, in relation to the combined weight of such base ingredients.

While this invention has been disclosed in considerable detail for purposes of illustration, it will be understood by those skilled in the art that many of such details may be varied without departing from the spirit and scope of the invention.

The invention claimed is:

1. An adhesive composition intended for adherence to the skin having relatively low cold flow and high cohesive strength, said composition comprising a network of entangled fibrillated polymeric fibers having a surface area of at least 4 m²/g, a continuous pressure-sensitive adhesive phase coating said fibers, and a discontinuous phase comprising particles of one or more liquid absorbing and swellable hydrocolloids dispersed throughout said network.

2. The composition of claim 1 in which said pressure-sensitive adhesive phase comprises polyisobutylene.

3. The composition of claim 2 in which said fibrillated fibers are comprised of polyolefin.

4. The composition of claim 3 in which said polyolefin comprises polyethylene.

5. The composition of any one of claims 1, 2 or 4 in which said surface area falls within the range of about 5 m²/g to about 20 m²/g.

6. The composition of claim 5 in which said fibers are composed of fibrils having an average length of about 0.1 to about 3 mm.

7. The composition of claim 5 in which said fibrils have an average diameter within the range of about 5 to about 50 microns.

8. The composition of claim 5 in which said hydrocolloids comprise a mixture of pectin and carboxymethylcellulose.

9. The composition of claim 8 in which said carboxymethylcellulose is sodium carboxymethylcellulose.

10. The composition of claim 8 in which said mixture comprises about 10% to 50% of the total weight of said composition.

11. The composition of claim 8 in which said mixture comprises about 5% to 20% pectin and about 5% to 30% carboxymethylcellulose of the total weight of said composition.

12. The composition of claim 8 in which said mixture comprises about 10% to 15% pectin and about 20% to 30% carboxymethylcellulose of the total weight of said composition.

13. The composition of claim 8 in which said mixture comprises about 13% pectin and about 25% carboxymethylcellulose of the total weight of said composition.

14. The composition of any one of claims 1, 2 or 3 in which said polyolefin is polyethylene and said fibrillated fibers constitute about 0.5% to about 6% by weight of said composition.

15. The composition of claim 1 in which said composition has a pH within the range of about 4 to 7 when said hydrocolloids are hydrated.

16. The composition of claim 2 in which said continuous phase includes medium molecular weight polyisobutylene having an average molecular weight within the range of about 10,000 to 40,000.

17. The composition of claim 16 in which said continuous phase includes low molecular weight polyisobutylene having an average molecular weight within the range of about 1,000 to 4,000.

18. The composition of claim 17 in which said low molecular weight polyisobutylene has an average molecular weight within the range of about 2,000 to 3,000.

19. The composition of claim 2 in which said continuous phase of polyisobutylene comprises 0% to about 65% medium molecular weight polyisobutylene, having an average molecular weight of about 10,000 to 40,000, per total weight of said composition, and 0% to about 80% low molecular weight polyisobutylene, having an average molecular weight of about 2,000 to 3,000, per total weight of said composition, wherein the total weight percent of the polyisobutylene content is at least 15% of the total weight of the composition.

20. The composition of claim 19 in which said composition comprises about 5% to 65% of said medium molecular weight polyisobutylene, about 3% to 60% of said low molecular weight polyisobutylene, about 1% to 3% of said fibrillated polyethylene, about 10% to 15% pectin, and about 20% to 30% of carboxymethylcellulose, of the total weight of said composition.

21. The composition of claim 19 in which said composition is a moldable skin barrier comprising about 50% to about 65% of said medium molecular weight polyisobutylene, 0% to about 10% of said low molecular weight polyisobutylene, about 10% to about 50% hydrocolloids, and about 0.5% to about 6% fibrillated polymeric fibers, per total weight of said composition.

22. The moldable skin barrier composition of claim 21 in which said composition comprises about 55% of said medium molecular weight polyisobutylene, about 5% of said low molecular weight polyisobutylene, about 2% fibrillated polyethylene fibers, about 13% pectin, and about 25% carboxymethylcellulose, per total weight of said composition.

23. The composition of claim 19 in which said composition is a paste comprising 0% to about 15% of said medium molecular weight polyisobutylene, about 40% to about 80% of said low molecular weight polyisobutylene, about 1% to about 3% of fibrillated polyethylene fibers, about 5% to 15% pectin, and about 10% to about 30% carboxymethylcellulose, per total weight of said composition.

24. The paste composition of claim 23 in which said composition comprises about 10% of said medium molecular weight polyisobutylene, about 50% of said low molecular weight polyisobutylene, about 2% of said fibrillated polyethylene fibers, about 13% pectin, and about 25% carboxymethylcellulose, per total weight of said composition.

25. The composition of claim 19 in which said composition is a paste containing a diluent for limiting the viscosity and promoting the moldability and flowability of said paste.

26. The paste composition of claim 25 in which said diluent is volatile.

27. The paste composition of claim 25 in which said diluent is non-volatile.

28. The paste composition of any one of claims 25, 26 or 27 having base ingredients comprising 0% to about 65% medium molecular weight polyisobutylene, 0% to about 10% low molecular weight polyisobutylene, about 0.5% to 6% fibrillated polyethylene fibers, about 1% to 15% pectin, and about 1% to 30% carboxymethylcellulose, in relation to the combined weight of said base ingredients, with the balance of said composition comprising said diluent.

* * * * *